United States Patent [19]
Feldman

[11] Patent Number: 5,485,269
[45] Date of Patent: Jan. 16, 1996

[54] SYSTEM FOR MINIMIZING NATIVE FIBER FLUORESCENCE VARIATIONS IN FIBER OPTIC SENSORS

[75] Inventor: Sandra F. Feldman, Schenectady, N.Y.

[73] Assignee: General Electric Company, Schenectady, N.Y.

[21] Appl. No.: 411,059

[22] Filed: Mar. 27, 1995

Related U.S. Application Data

[63] Continuation of Ser. No. 250,234, May 27, 1994, abandoned, which is a continuation-in-part of Ser. No. 36,573, Mar. 24, 1993, Pat. No. 5,399,866.

[51] Int. Cl.$^6$ ............................................. G01J 3/30
[52] U.S. Cl. ................... 356/318; 250/458.1; 250/459.1
[58] Field of Search ............................ 356/317, 417, 356/318; 250/458.1, 459.1, 461.1

[56] References Cited

U.S. PATENT DOCUMENTS

| | | | |
|---|---|---|---|
| 4,648,892 | 3/1987 | Kittrell et al. | 65/4.21 |
| 4,929,561 | 5/1990 | Hirschfeld | 250/459.1 |
| 4,945,245 | 7/1990 | Levin | 250/459.1 |
| 5,061,857 | 10/1991 | Thompson et al. | 250/458.1 |
| 5,084,617 | 1/1992 | Gergely | 250/461.1 |
| 5,315,993 | 5/1994 | Alcala | 250/458.1 |

OTHER PUBLICATIONS

"Comparative Analysis of Toxin Detection in Biological and Environmental Samples" by Ogert, et al, SPIE Vol. 2068, pp. 151–158.

"Fiber–Optic Chemical Sensors for Competitive Binding Fluoroimmunoassay" by Tromberg, et al, Anal. Chem. 1987, vol. 59, pp. 1226–1230.

*Primary Examiner*—Robert P. Limanek
*Assistant Examiner*—David B. Hardy
*Attorney, Agent, or Firm*—Ann M. Agosti; Marvin Snyder

[57] ABSTRACT

An optical system for minimizing native fluorescence variations from a fiber optic laser induced fluorescence sensor comprises a fiber probe for receiving excitation light which is capable of guiding excitation light to an analyte and coupling fluorescence from the analyte to a detector and an excitation light director for selectively supplying the excitation light to the fiber probe during a plurality of predetermined measurement periods. The excitation light director includes a light source which may itself be programmable or a light source in combination with a programmable shutter or beam deflector.

16 Claims, 1 Drawing Sheet

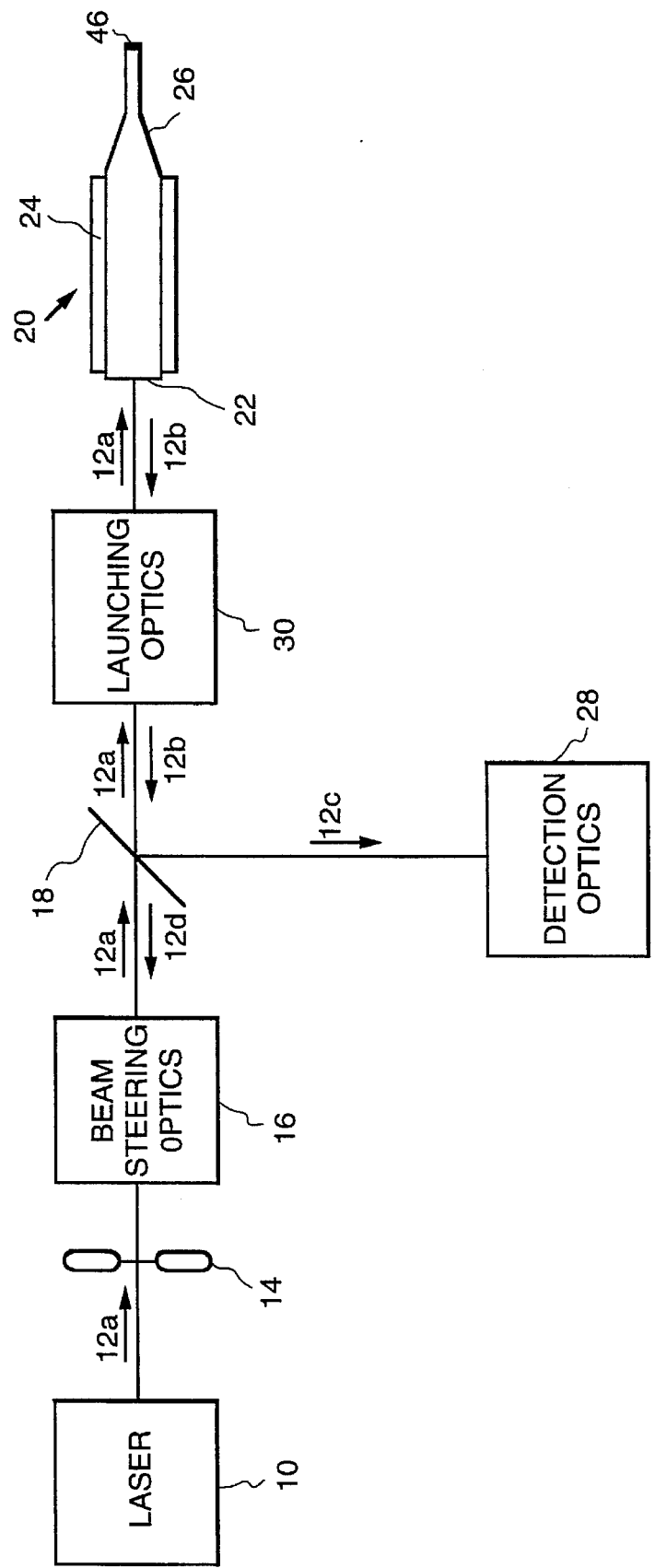

SYSTEM FOR MINIMIZING NATIVE FIBER FLUORESCENCE VARIATIONS IN FIBER OPTIC SENSORS

CROSS REFERENCE TO RELATED APPLICATION

This application is a Continuation of application Ser. No. 08/250,234, filed 27 May 1994, now abandoned, which is a continuation-in-part of application Ser. No. 08/036,573, filed Mar. 24, 1993, now U.S. Pat. No. 5,399,866.

BACKGROUND OF THE INVENTION

1. Field of the Invention

This invention relates generally to fiber optic fluorescence sensing, and, more particularly, to a shutter system for minimizing background variation in a fiber optic laser induced fluorescence sensor (LIFS).

2. Description of the Related Art

In a fiber optic based LIFS probe, an energy field propagates through a fiber to an active region. In the active region, evanescent or distal field excitation leads to a fluorescent signal from an analyte outside the fiber. The fluorescent signal propagates back through the fiber and is used to estimate the concentration of the analyte. Typical uses for such probes include detecting hazardous waste and monitoring the contamination of a process stream.

When using fiber optic spectroscopic sensors, it is common and desirable to transmit the excitation laser beam and the returning spectroscopic signal through the same fiber. Often the excitation beam excites native fluorescence in the fiber. Because in many systems it is impossible to filter the native fiber fluorescence from the signal due to overlapping spectra, the native fiber fluorescence will be detected and must be subtracted from the signal of interest. In many fibers the native fluorescence will slowly diminish in time as a result of continuous exposure to excitation light. This time-varying signal is difficult to quantify and subtract properly from the signal of interest, and thus degrades system performance.

As discussed in Bruce J. Tromberg et al., "Fiber-Optic Chemical Sensors for Competitive Binding Fluoroimmunoassay," Analytical Chemistry 59, 1226–30 (1987), in systems using dye labeled chemicals as part of the detection process, a hand operated shutter has been used to prevent fluorescent dye photodegradation and to enhance fiber-to-fiber reproducibility. This description does not address the problem of time-varying native fluorescence, however.

As described in Robert A. Ogert et al., "Comparative Analysis of Toxin Detection in Biological and Environmental Samples," SPIE Vol. 2068, 151–158 (1994), one attempt to minimize the native fluorescence has been to photobleach fluorescent components within the fiber itself until the fiber has a stable background drift over the time required to make the measurement. This technique generally requires pre-exposing the fibers to excitation light for approximately ten minutes immediately prior to use before any measurement is made. The fibers cannot be pre-exposed during their fabrication process because the photodegradation is a reversible process and the native fiber fluorescence will recover during fiber storage. The need to expose fibers to excitation light for a substantial period of time immediately prior to their use imposes a stringent limit on the field portability and use of any instrument requiring the fibers. Furthermore, if the measurement periods will require more than several minutes, longer pre-exposure times are required.

SUMMARY OF THE INVENTION

Accordingly, an object of the invention is to minimize changes in a background signal due to native fiber fluorescence in single fiber transmission-reception configurations. In particular, the invention minimizes changes which occur as a result of extended exposure to exaltation light.

Briefly, according to a preferred embodiment of the invention, a method for reducing the variation in native background fluorescence of fiber optic sensors in order to improve signal to noise ratio and reduce detection limits uses a programmable shutter (or other means) to expose the fiber to excitation light only when data is being taken instead of continuously flooding the fiber sensor with excitation light.

According to another preferred embodiment of the invention, an optical system for minimizing native fluorescence lo variations from a fiber optic laser induced fluorescence sensor comprises a light source for providing excitation light; a fiber probe capable of guiding excitation light to and coupling fluorescence from an analyte; and a programmable excitation light director between the light source and the fiber probe for selectively supplying the excitation light to the fiber probe during a plurality of predetermined measurement periods. The programmable excitation light director is selected from the group consisting of a shutter and a beam deflector.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawings, in which:

FIG. 1 is a schematic diagram of an embodiment of the present invention.

DETAILED DESCRIPTION OF A PREFERRED EMBODIMENT OF THE INVENTION

In FIG. 1, a light source, shown as a laser 10, supplies excitation light for inducing fluorescence and may comprise, for example, either a continuous wave (CW) or pulsed laser. In a preferred embodiment, the light source comprises a CW argon laser with a wavelength of 488 nm. Other light sources can be used such as, for example, an arc lamp. Steering mirrors, used to position the optics more efficiently on a table, are not shown. Laser 10 supplies the excitation light along a path 12a towards a fiber probe 20.

An excitation light director, shown as electronic shutter 14, is used to limit the exposure of light to the fiber to the times when data is taken. Preferably the electronic shutter is a programmable shutter, such as fabricated by Vincent Associates and sold under the name Uniblitz® Electronic. The shutter is useful because the background signal drops with time when the fiber is exposed continuously to laser light. By limiting the fiber exposure and allowing the fiber to recover between exposures, the background becomes more constant.

Depending on the time scale of the reaction being observed, different programs can be used to control the shutter. For slow reactions, example exposure times are: 10 seconds per minute for a 10 minute period; 10 seconds per two minutes for a 20 minute period; and 10 seconds per 5 minutes for an indefinite period thereafter.

For faster reactions in which too much data would be lost in the first minute, or for reactions in which it is desirable to measure the initial slope of the signal response, the fiber is exposed continuously for the first minute of the reaction followed by the sequence specified above for slow reactions.

Other excitation light directing techniques for limiting exposure of light can be used with the present invention. For example, a laser such as a laser diode can itself be modulated by turning it on only when taking a measurement. Preferably any such laser is controlled by a computer program.

In another example, a beam deflector can be used to control the supply of light to fiber probe 20. The beam deflector can be programmed or otherwise controlled to direct excitation light in the direction of the fiber only when measurements are to be taken. Preferably an optical stop including an aperture is positioned between the beam deflector and the fiber probe to minimize any stray light. If an electro-optic or acousto-optic beam deflector is used, the deflector will respond to a respective electrical or acoustical signal by deflecting excitation light through the aperture. In the absence of a respective signal, the fiber remains unexposed. In another example, a beam deflector is formed using a mechanically rotated mirror or a prism wedge to allow the laser beam to reach the fiber only during the measurement time.

After the excitation light has passed through shutter 14, the light is passed through beam steering optics 16 which supply light to fiber probe 20 through a beam splitter 18.

Launching optics 30 can additionally be present between the beam splitter and the fiber probe, if desired. In other embodiments, beam steering optics 16 can perform both the beam steering and launching functions without launching optics 30, or beam steering optics 16 can be omitted.

For evanescent field sensing, fiber probe 20 (shown with an exaggerated thickness) preferably comprises quartz and has a tapered fiber core 26 at the end opposite the the entrance of the excitation light. A preferred method for tapering fibers and preferred fiber profiles are described in commonly assigned U.S. Pat. No. 5,290,398, issued Mar. 1, 1994. The fiber core can be partially surrounded by fiber cladding 24 which may also comprise quartz having a lower index of refraction than the index of refraction of the fiber core. If the fiber sensor is of the evanescent type, then preferably the fiber is designed so that excess light transmitted through the probe is absorbed on a fiber back face 46 by, for example, black epoxy coated thereon. For a distal fiber sensor, neither the taper nor an absorbing medium is necessary. If the fiber is properly oriented, any laser light which is reflected from a fiber probe front face 22 is directed back through the beam splitter along paths 12b and 12d and is not directed into detection optics 28.

Fluorescence detected in the fiber probe is also sent back along path 12b to the beam splitter which preferably directs a large portion of the florescence to the detection optics along light path 12c.

Any conventional launching and detection optics can be used. Preferred examples of launching and detection optics can be found in the aforementioned related Application Ser. No. 08/036,573. The detection optics are not limited to photodetectors and can include, for example, spectral filters or signal discriminating electronics such as lock-in amplifiers.

While only certain preferred features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. An optical system in which native fluorescence variations from a fiber optic laser induced fluorescence sensor are minimal, the optical system comprising:

a fiber probe for receiving excitation light, the fiber probe capable of guiding excitation light to an analyte; and excitation means for selectively supplying the excitation light to the fiber probe during a plurality of predetermined varying measurement periods separated by intervals in which said excitation light is not supplied, said intervals being long enough to allow a background signal of the fiber probe to recover so as to minimize said native fluorescence variations from the fiber optic laser induced fluorescence sensor, said fiber probe being adapted to couple fluorescence from the analyte during said plurality of predetermined measurement periods.

2. The system of claim 1, wherein the excitation means comprises programmable excitation means.

3. The system of claim 1, wherein the excitation means includes a light source.

4. The system of claim 3, wherein the light source comprises a laser.

5. The system of claim 3, wherein the excitation means includes a shutter between the light source and the fiber probe.

6. The system of claim 3 further including means for controlling the light source with a computer program.

7. The system of claim 3, wherein the predetermined varying measurement periods are selected to occur at 10 seconds per minute for a 10 minute period, 10 seconds per 2 minutes for a 20 minute period, and 10 seconds per 5 minutes for a remainder of the predetermined varying measurement periods.

8. The system of claim 3 wherein the excitation means includes a beam deflector between the light source and the fiber probe.

9. The system of claim 8, wherein the beam deflector is one selected from a group consisting of an electro-optic beam deflector and an acousto-optic beam deflector.

10. The system of claim 8, wherein the beam deflector is one selected from a group consisting of a rotating mirror beam deflector and a prism wedge beam deflector.

11. An optical system in which native fluorescence variations from a fiber optic laser induced fluorescence sensor are minimal, the optical system comprising:

a light source for providing excitation light;

a fiber probe for receiving the excitation light, the fiber probe capable of guiding excitation light to an analyte; and a programmable excitation light director between the light source and the fiber probe for selectively supplying the excitation light to the fiber probe during a plurality of predetermined varying measurement periods separated by intervals in which said excitation light is not supplied, said intervals being long enough to allow a background signal of the fiber probe to recover so as to minimize said native fluorescence variations from the fiber optic laser induced fluorescence sensor, said fiber probe being adapted to couple fluorescence from the analyte during said plurality of predetermined measurement periods, the programmable excitation light director is one selected from a group consisting of a shutter light director, a laser modulating light director, and a beam deflector light director.

12. A method in which native fluorescence variations from a fiber optic laser induced fluorescence sensor are minimal, the method comprising selectively supplying excitation light to a fiber probe capable of guiding the excitation light to and coupling fluorescence from an analyte during a plurality of predetermined varying measurement periods separated by intervals in which said excitation light is not supplied, said intervals being long enough to allow a background signal of the fiber probe to recover so as to minimize said native fluorescence variations from a fiber optic laser induced fluorescence sensor.

13. The method of claim 12, wherein the supplying of excitation light comprises supplying light from a programmable laser.

14. The method of claim 12, wherein the supplying of excitation light includes supplying the excitation light from a light source through a programmable shutter.

15. The method of claim 12, wherein the supplying of excitation light includes supplying the excitation light from a light source through a programmable beam deflector.

16. The method of claim 12, wherein the supplying of excitation light at predetermined varying measurement periods occurs at 10 seconds per minute for a 10 minute period, 10 seconds per 2 minutes for a 20 minute period, and 10 seconds per 5 minutes for a remainder of the predetermined varying measurement periods.

* * * * *